United States Patent [19]

Budai et al.

[11] 4,310,348
[45] Jan. 12, 1982

[54] PLANT GROWTH REGULATING COMPOSITIONS

[75] Inventors: Zoltán Budai; Ferenc Jurák, both of Budapest; Attila Kis-tamas, Pilisvorosvar; Aranka Lay née Konya, Budapest; Tibor Mezei, Budapest; Zoltan Vig, Budapest; Terez Zubovits nee Kristof, Budapest, all of Hungary

[73] Assignee: Egyt Gyogyszervegyeszeti Gyar, Budapest, Hungary

[21] Appl. No.: 166,975

[22] Filed: Jul. 9, 1980

Related U.S. Application Data

[62] Division of Ser. No. 65,156, Aug. 9, 1979, Pat. No. 4,244,888.

[30] Foreign Application Priority Data

Aug. 22, 1978 [HU] Hungary .............................. EE 2589

[51] Int. Cl.³ .................................................. A01N 33/02
[52] U.S. Cl. ........................................ 71/121; 111/77; 111/DIG. 1
[58] Field of Search ................................. 71/121, 77

[56] References Cited

U.S. PATENT DOCUMENTS 3,733,359  5/1973  Hubele ................... 71/121
3,989,737  11/1976  Sawaki et al. ........... 71/121
4,052,194  10/1977  Wilcox .................... 71/94

FOREIGN PATENT DOCUMENTS 7118093  7/1972  Netherlands ............. 71/121
1226933  3/1971  United Kingdom ..... 71/77

Primary Examiner—Glennon H. Hollrah
Attorney, Agent, or Firm—Young & Thompson

[57] ABSTRACT

Racemic or optionally active 2-(propargyloxyimino)-1,7,7-trimethyl-bicyclo[2,2,1]heptane of the formula (I)

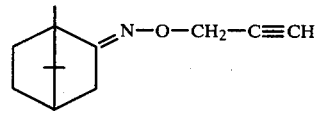

(I)

or a mixture of these isomers is prepared by reacting a racemic or optically active 1,7,7-trimethyl-bicyclo[2,2,1]heptane derivative of the general formula (II),

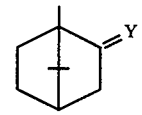

(II)

wherein
Y stands for oxygen atom, sulfur atom or oxime group, with a propyne derivative of the general formula (III),

R—CH₂—C≡CH  (III)

wherein
R stands for halogen atom or aminooxy group, with the proviso that if Y represents oxime group, R may stand only for halogen, and if R represents aminooxy group, Y may stand only for oxygen or sulfur atom.

The resulting product is new and possesses strong plant growth promoting and insecticidal effects.

1 Claim, No Drawings

PLANT GROWTH REGULATING COMPOSITIONS

This is a division of application Ser. No. 065,156, filed Aug. 9, 1979, now U.S. Pat. No. 4,244,888, Jan. 13, 1981.

The invention relates to plant growth regulating compositions containing racemic or optically active 2-(proparglyoxyimino)-1,7,7-trimethyl-bicyclo[2,2,1-]heptane of the formula (I),

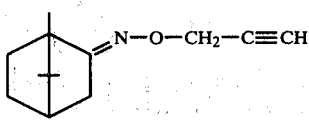
(I)

or a mixture thereof as active agent, as well as the utilization of such compositions in agriculture, horticulture or forestry. The invention relates further to the new compound of the formula (I), as well as to a process for the preparation of this compound. In the specification and claims the term "a compound of the formula (I)" relates to the racemate, the pure optically active isomers and any isomeric mixture of the new compound concerned.

Plant growth regulating substances have been used in the agriculture and horticulture for about 40 years. A comprehensive review of these compounds was first published by S. H. Wittwer in 1971 (S. H. Wittwer: Outlook on Agriculture 6, 205 (1971)).

The known plant growth regulating substances can be classified into two groups, i.e. natural and synthetic substances.

The natural plant growth promoting agents are auxines, gibberellines and cytoquinines, whereas the natural plant growth inhibiting agents are the abscisic acids (ABS) first reported in 1965 (R. Wegler: Chemie der Pflanzenschutz-und Schädlingsbekämpfungsmittel, pp. 399–429 (Springer Verlag, Berlin-Heidelberg-New York, 1970)).

The plant growth promoting effects of some inorganic salts have also been investigated quite recently. The published German patent specification No. 1,932,198 describes plant growth promoting compositions containing polyphosphates, polyphosphorous acid esters, ceric nitrate, other known cerium compounds or mixtures thereof.

In the last few years several attempts have been made to prepare synthetic organic compounds capable of a controlled promotion of the natural growth of plants without exerting harmful side effects, such as deformation or premature destruction of the plant. Although a considerable progress can be observed in this field, the problems have not been solved yet (R. Wegler: Chemie der Pflanzenschutz-und Schädlingscbekämpfungsmittel. Natürliche und syntetische Pflanzenwachstumsregulatoran. Vol. 4, pp. 47–48 (Springer Verlag, Berlin-Heidelberg-New York, 1977)).

The invention aims at providing a new and easily available plant growth regulating agent, which promotes the natural growth of plants in a controlled manner, without leading to the deformation or premature destruction of the plants treated.

Now it has been found that 2-(propargyloxyimino)-1,7,7-trimethyl-bicyclo[2,2,1]heptane of the formula (I), a new compound synthetized first by the inventors, exerts particularly advantageous and unexpected effects in plant protection. This compound promotes not only the germination of plants, but exerts a growth promoting effect in the vegetative development stage of plants as well, moreover it has a marked crop yield increasing effect in the generative phase.

As known, in higher dosages, plant growth promoting agents exert herbicidal effects (B. T. Brown: Pestic. Sci. 3, 161 (1971)). The relationship of these two effects is characterized by the activity index, which is the ratio of the minimum lethal concentration to the minimum plant growth influencing concentration of the substance concerned. Thus it is known that plant growth promoting agents can be applied as herbicides in higher dosages. It is, however, very surprising that the new compound of the formula (I) possesses, in addition to its plant growth regulating effect, insecticidal activity.

A further advantage of the new compound is its low toxicity and the absence of cholinesterase blocking effects, which make it innocuous for humans and warm-blooded animals. Therefore, the new compound of the formula (I) can be utilized to advantage as insecticidal agent for controlling granarial insect pests and insects attacking ornamental plants, indoor plants and vegetables. The $LD_{50}$ value of $(\pm)$-2-(propargyloxyimino)-1,7,7-trimethyl-bicyclo[2,2,1]-heptane, determined on white rats after oral administration, is 1400 mg/kg.

The new compound of the formula (I) is prepared according to the invention by reacting a racemic or optically active 1,7,7-trimethyl-bicyclo[2,2,1]heptane derivative of the general formula (II),

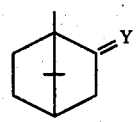
(II)

wherein Y stands for oxygen atom, sulfur atom or oxime group, with a propyne derivative of the general formula (III) or an acid addition salt thereof,

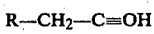  (III)

wherein R stands for halogen or aminooxy group, with the proviso that if Y represents oxime group, R may stand only for halogen, and if R represents aminooxy group, Y may stand only for oxygen or sulfur atom, separating the resulting product from the reaction mixture, and, if desired, resolving the racemic product.

The term "halogen" used in connection with the definition of R covers fluorine, chlorine, bromine and iodine.

The compounds of the general formulae (II) and (III), applied as starting substances in the preparation of the new compound according to the invention, are known substances.

The above reaction is performed in an inert solvent or—preferably—in a mixture of inert solvents, in the presence of a basic condensing agent.

Of the inert solvents usable in the reaction aromatic hydrocarbons (such as benzene, toluene, xylene, etc.), open-chain ethers and cyclic ethers (such as dibutyl ether, dioxane, tetrahydrofuran, etc.), dipolar aprotic solvents (such as dimethyl acetamide, dimethyl formamide, etc.) and aliphatic alcohols (such as methanol, ethanol, isopropanol, etc.) are to be mentioned.

The reaction can be performed to advantage in a mixture of two different inert solvents, such as in a mixture of toluene and dimethyl acetamide, xylene and dimethyl formamide, toluene and dimethyl formamide, etc. The use of a mixture of xylene and dimethyl formamide proved to be particularly preferable, since in this instance the inorganic salts formed in the reaction and dimethyl formamide can easily be removed from the mixture at the end of the reaction by treating the reaction mixture with water. The resulting xylene solution of the racemic or optically active compound having the formula (I) can be utilized directly, i.e. without separating the active agent, in the preparation of emulsifiable concentrates.

When a compound of the general formula (II), wherein Y stands for oxygen or sulfur atom, is used as starting substance, generally an organic base, preferably pyridine, is utilized as basic condensing agent. When the compound of the general formula (I) is prepared from the corresponding oxime of the general formula (II), an alkali metal hydroxide, alkoxide, amide or hydride can be used as basic condensing agent. Of the alkali metal compounds sodium derivatives are preferred. Other alkali metal compounds can be used as well, they have, however, no advantage over the sodium derivatives.

The racemic or optically active compound of the formula (I) or their mixture can be converted into plant growth regulating and/or insecticidal compositions, such as emulsifiable concentrates (EC), granulates (preferably microgranulates), foils (such as sowing-seed foils), etc. These compositions contain the racemic or optically active new compound or their mixture (in the following: "active agent") in combination with solid or liquid inert carriers or diluents, solvents and other auxiliary agents.

Of the auxiliary agents e.g. surfactants (such as wetting, emulsifying and dispersing agents), anticaking agents, lubricants, adhesives, sticking aids, dyestuffs, corrosion inhibitors, suspending agents, substances increasing the resistance against rain, penetration aids, etc. are to be mentioned.

As solid carriers or diluents e.g. inert mineral substances, such as aluminum silicate, talc, ignited magnesia, silica, tricalcium phosphate, cork meal, coke powder, clays, kaolin, pearlite, pyrophillite, dolomite, gypsum, calcium phosphate, calcium carbonate, mica, colloidal silicon dioxide, Fuller's earth, Hewitt's earth, china clay, etc. can be applied.

As liquid carriers or diluents e.g. aqueous, organic and/or aqueous-organic solvents, such as water, ketones (e.g. acetophenone, cyclohexanone, isophoron, etc.), aromatic hydrocarbons (e.g. benzene, toluene, xylene, etc.), alkylnaphthalenes, tetrahydronaphthalene, chlorinated hydrocarbons (e.g. chlorobenzenes, dichloroethylene, trichloroethylene, tetrachloroethane, etc.), alcohols (e.g. methanol, ethanol, isopropanol, butanol, propylene glycol, diacetone alcohol, etc.), kerosene, mineral, animal and vegetable oils, aliphatic mineral oil fractions, petrol distillates with high aromatic contents (e.g. naphtha and distilled tar oil), polar organic solvents (e.g. dimethyl sulfoxide and dimethyl formamide), and mixtures thereof can be applied.

Besides the solid and liquid carriers mentioned above inert gaseous carriers can be applied as well. Of the gaseous carriers and Freon-type gases; such as various chlorinated or fluorinated methane and ethane derivatives (e.g. fluorodichloromethane, difluorodichloromethane, etc.) are to be mentioned.

The wetting, dispersing and emulsifying surfactants can be ionic or non-ionic in type.

As non-ionic surfactants e.g. condensates of ethylene oxide with $C_{10-20}$ fatty alcohols (such as oleyl alcohol, cetyl alcohol, octadecyl alcohol, etc.), alkylphenols (such as octylphenol, nonylphenol, octylcresol, etc.), amines (such as oleylamine), mercaptans (such as dodecylmercaptan) or carboxylic acid, partial esters of higher fatty acids and hexitol anhydrides, condensation products of these partial esters and ethylene oxide, lecithins, fatty acid esters of polyalcohols, etc. can be applied.

The ionic surfactants can be cationic or anionic compounds.

Of the cationic surfactants e.g. the quaternary ammonium compounds (such as cetyl-trimethyl-ammonium bromide, cetylpyridinium bromide, etc.) are to be mentioned.

Examples of the anionic surfactants are soaps, salts of aliphatic monoesters of sulfuric acid (such as sodium laurylsulfate, sodium salt of dodecanol monosulfate), salts of sulfonated aromatic compounds (such as sodium dodecyl benzenesulfonate, sodium-, calcium- or ammonium ligninsulfonate), butylnaphthalenesulfonate, mixtures of the sodium salts of di- and triisopropyl-naphthalenesulfonic acid, sodium salts of petroleumsulfonic acids, potassium or triethanolamine salts of oleic acid or abietic acid, etc. As suspending agents e.g. hydrophilic colloids (such as polyvinyl pyrrolidone, sodium carboxymethyl cellulose, etc.), furthermore gums of vegetable origin (such as traga-canth gum, etc.) can be applied.

Examples of sticking aids are lubricants (such as calcium or magnesium stearate), adhesives (such as polyvinyl alcohol), cellulose derivatives and other colloidal substances (such as cassine), mineral oils, etc.

Of the dispersing agents e.g. methyl cellulose, ligninsulfonates, alkylnaphthalenesulfonates, etc. are to be mentioned.

As distribution aids, sticking aids, agents for increasing rain resistance or penetration aids e.g. fatty acids, resins, glue, casein and alginates can be applied.

Utilizing the carriers, diluents and auxiliary agents mentioned above, the active agent according to the invention can be converted into various solid, liquid or gaseous agricultural or horticultural compositions.

Examples of the solid compositions are grains and granulates (preferably microgranulates), pastes, granulated, dressed or—preferably—coated seeds, agricultural (primarily horticultural) sowing-seed foils, etc.

Of the liquid compositions the following are to be mentioned: solutions, such as directly sprayable solutions (e.g. aqueous solutions, solutions formed with organic solvents or oils, miscible oils, etc.), dispersions, suspensions (primarily aqueous suspensions), aqueous or oily emulsions, invert emulsions, etc.

As gaseous compositions e.g. aerosol preparations can be applied.

The granular compositions can be prepared e.g. by dissolving the plant growth regulating agent of the invention in a solvent, and applying the solution onto a granular carrier (e.g. a porous granular substance, such as pumice stone or attaclay, a non-porous granular mineral substance, such as sand or loam, or a granular organic substance, such as black soil or cut tobacco stalk) in the presence of a binding agent, and, if desired, drying the resulting granular substance. According to another method, granular compositions are prepared by admixing the plant growth regulating agent with a powdered mineral substance, a lubricant and a binding agent, compressing the mixture, crushing the compressed substance, and separating the fraction with the required grain size by sieving. A preferred method of preparing granular compositions in dry or wet granulation, the latter being performed either by wet compression or by buildup technique.

A particularly preferred form of the compositions is the sowing-seed foil. As well known, in order to facilitate the sowing of seeds and to ensure uniform distances between the individual seeds and rows, manual sowing or planting is increasingly replaced in the agriculture (primarily in the horticulture) by incorporating the seeds into a water-soluble foil, and placing the resulting foil bands, which contain optionally more than one row of seeds, into the soil. The foil can be made of any water-soluble substance inert towards the seeds, such as polyvinyl alcohol; the only requirement is that the foil does not damage the seeds and disintegrates or dissolves in the soil upon the effect of moisture. The sowing-seed foil according to the invention may contain the new active agent incorporated into the foil material, or seeds pre-treated with the new active agent can be incorporated into the foil. It is a particular advantage of the sowing-seed foils that the new active agent increases primarily the germination ability of the seeds in the foil and then promotes primarily the growth of the plants to be cultivated, also providing an appropriate protection against insect pests during the initial development of the plants.

Dispersions, suspensions or emulsions can be prepared by dissolving or suspending the active agent according to the invention in a solvent which contains optionally one or more wetting, dispersing, suspending and/or emulsifying agent(s), and admixing the resulting mixture with water, also containing optionally one or more wetting, dispersing, suspending and/or emulsifying agent(s). Of course, either the solvent or the water applied must contain at least one wetting, dispersing, suspending and/or emulsifying agent.

Miscible oils can be prepared by dissolving or finely dispersing the active agent according to the invention in an appropriate solvent, preferably in a solvent slightly miscible with water, in the presence of an emulsifying agent.

Solutions for direct spraying are prepared by dissolving the active agent according to the invention in a solvent with medium to high boiling point. It is preferred to apply a solvent boiling above 100° C.

Aerosols can be prepared e.g. by admixing the active agent according to the invention, or—if necessary—a solution thereof, with a volatile liquid applied as propellant, e.g. with a Freon-type compound.

Invert emulsions can be prepared by emulsifying an emulsion of the active agent according to the invention in water directly in the spraying apparatus either before or during spraying.

Emulsifiable concentrates, pastes or wettable spray powders can be applied particularly preferably to prepare aqueous formulations ready for use. These concentrates are diluted prior to use with water to the required concentration. The concentrates should be stable for a prolonged period of storage, and, after dilution with water, they should form aqueous compositions which remain homogeneous for a time sufficient to apply them with a conventional spraying apparatus. The concentrates generally contain 10 to 85% by weight, preferably 25 to 60% by weight, of active agent. The dilute aqueous compositions (spray liquids) ready for use contain preferably 0.001 to 3.00% by weight of active agent, however, for specific applications, compositions with higher or lower active agent content can also be prepared.

Depending on the method of preparation and application, the active agent contents of the compositions required to have the desired effect may vary over a broad range. The compositions contain generally 0.01 to 95% by weight of active agent. When the composition is to be applied according to the "ultra-low volume" (ULV) technique, the active agent according to the invention can be admixed with extremely small amounts of additives to form compositions containing preferably 90 to 98% by weight of active agent. These compositions are applied to the desired places with an apparatus producing extremely fine sprays, preferably from an aeroplane. Diluted compositions contain generally 0.01 to 20% by weight of active agent, whereas the active agent content of concentrates may vary generally between 20 and 98% by weight.

The emulsifyable concentrates contain generally 5 to 70% by weight, preferably 10 to 50% by weight, of active agent. The active agent content of powdery compositions may be generally 0.5 to 10% by weight, preferably 1 to 5% by weight.

The compositions according to the invention can be applied as sprays, powder sprays, coating agents (e.g. for seed coating), sowing-seed foils, soil watering compositions, dip-in baths, etc. The type of composition to be applied depends on the requirements of the field of application.

The invention relates further to an agricultural process, in which the plants, seeds and/or the soil is (are) treated either directly or indirectly with a composition containing a racemic or optically active compound of the formula (I) or their mixture.

In this agricultural process the compositions according to the invention are applied onto or into the soil, onto the seeds or plants, or onto a pre-selected part of the plants.

Seeds can be treated e.g. by coating them with the active agent according to the invention, optionally along with a carrier, under stirring. The active agent of the invention can also be applied onto seeds along with wetting surfactants as defined above and optionally with a carrier. In this latter instance the mixture of the active agent, surfactant and carrier is wetted first with a small amount of water, and the seeds are admixed with the resulting suspension.

A specific method of seed treatment is seed coating according to the dragée-producing technique. This can be performed e.g. by placing the seeds into a dragée pan, rotating the pan, and wetting the seeds with an aqueous solution of a binding agent (e.g. sodium carboxymethyl cellulose). Thereafter the coating agent, a powdery mixture, is sprayed onto the surface of the wet seeds. The coating agent is administered until the required final weight or dimension of the coated seed is reached.

The agricultural process according to the invention can also be performed so that the active agent is admixed with soil, sand or another powdered solid carrier listed above and optionally with a surfactant, and the resulting powder mixture is applied into the furrows during sowing.

The active agent can be applied onto the seeds prior to, simultaneously with, or after sowing, either according to the agricultural methods discussed above, or in the form of an aqueous spray containing the active agent optionally along with a surfactant and/or a powdered solid substance as defined above.

The agricultural treatment method of the invention can also be performed by applying the composition containing the active agent directly to the plant, to certain parts (e.g. the leaves) of the plants, or to the environment of the plants. The compositions can be applied to the desired place e.g. by spraying, dusting, etc. The compositions can also be applied into the soil, e.g. by watering, flooding or incorporation techniques. According to the latter, the seeds are sown into furrows pre-treated with the composition in question.

The compositions according to the invention can be used for regulating the growth of both monocotyledons and dicotyledons. Pre-sowing, pre-planting, pre-emergent and post-emergent treatment methods, furthermore incorporation into soil can equally be applied.

The term "pre-sowing" or "pre-planting" means that the compositions according to the invention are applied onto the soil first, and sowing or planting is performed after this operation.

The term "pre-emergent treatment" means that the compositions according to the invention are applied onto the soil prior to plant emergence, e.g. by spraying the soil before the germinating plants break through the soil surface.

The term "post-emergent treatment means that the compositions according to the invention are applied onto the area to be treated (e.g. onto the plants or soil) after the plants have emerged.

According to our experiences the compositions of the invention are particularly useful in regulating the growth of corn, cereals, sunflower, alfalfa, sugar beet, rape, soybean, potato, rice, green pepper, tomato and vegetables.

The dosage of the active agent required to attain the desired plant growth regulating and/or insecticidal effect depends on several factors, such as the optical activity of the active agent (racemic, dextrorotatory, laevorotatory), the type and general state of the cultivated plant to be treated or of the insect to be combatted, the development stage of the cultivated plant (seed, germinating seedling, 1 to 3 leaves' stage, etc.), the type of other plants growing in the environment of the plant to be treated, the season, meteorological conditions, the method of applying the composition (pre-emergent, pre-sowing, pre-planting, post-emergent, incorporation into soil, etc.), and on the actual form of the composition. Accordingly, the optimum dosage should always be determined empirically. The active agent is generally applied in a dosage of 0.1 to 25 kg/hectare, preferably 0.1 to 15 kg/hectare. The optimum dosage of seed dressing or germination promoting is about 5 to 500 g/100 kg of seeds. When plant growth promoting or crop yield increasing effect is desired, or soil treatment is performed, the optimum dosage varies between 0.1 and to 15 kg/hectare. The optimum insecticidal dosage for seed treatment is about 1 to 10,000 ppm.

The final concentration of the diluted compositions ready for use also depends on the field of application (e.g. seed treatment, treatment of leaves, application onto soil, incorporation into soil, etc.). Thus e.g. diluted compositions containing 0.5 to 10,000 ppm, preferably 1 to 1000 ppm, of active agent are applied for seed and leaf treatment, as well as to increase germination power, whereas pre-emergent and post-emergent treatments are performed with diluted compositions (e.g. spray liquids) generally containing 0.1 to 3.0% by weight, preferably 0.3 to 1.0% by weight, of active agent.

The invention is elucidated in detail by the aid of the following non-limiting Examples.

EXAMPLE 1

Preparation of (±)-2-(propargyloxyimino)-1,7,7-trimethyl-bicyclo[2,2,1]heptane 4.6 g (0.2 mole) of metallic sodium are dissolved in 200 ml of methanol, and 33.4 g (0.2 mole) of (±)-1,7,7-trimethyl-bicyclo[2,2,1]heptane-2-one-oxime are added to the solution. After one hour of boiling 23.8 g (0.2 mole) of propargyl bromide are introduced, and the reaction is continued for a further hour. The mixture is cooled, the separated sodium bromide is filtered off, the filtrate is concentrated, and the concentrate is subjected to fractional distillation in vacuo. 33.2 g (81%) of (±)-2-(propargyloxyimino)-1,7,7-trimethyl-bicyclo[2,2,1]heptane are obtained as a light yellow oil; b.p.: 94° C./1.5 mm Hg, $n_D^{20}=1.4955$.

Analysis: Calculated for $C_{13}H_{19}NO$: C: 76.05%, H: 9.33%, N: 6.82%; Found: C: 76.17%, H: 9.62%, N: 6.88%.

EXAMPLE 2

Preparation of (±)-2-(propargyloxyimino)-1,7,7-trimethyl-bicyclo[2,2,1]heptane 4.8 g (0.2 mole) of sodium hydride are added to 150 ml of dry benzene, and a solution of 33.4 g (0.2 mole) of (±)-1,7,7-trimethyl-bicyclo[2,2,1]heptane-2-one-oxime in 50 ml of dimethyl formamide is introduced into the mixture at 50° C. within 0.5 hours. When gas evolution ceases, the mixture is cooled to 25° C., and 23.8 g (0.2 mole) of propargyl bromide are added. The reaction is continued for an additional 2 hours. Thereafter the reaction mixture is shaken with water, the phases are separated, the benzene phase is evaporated, and the residue is subjected to fractional distillation in vacuo. 37.0 g (90.5%) of (±)-2-(propargyloxyimino)-1,7,7-trimethyl-bicyclo[2,2,1]heptane are obtained as a light yellow oil; b.p.: 94°–96° C./1.5 mm Hg, $n_D^{20}=1.4953$.

EXAMPLE 3

Preparation of (±)-2-(propargyloxyimino)-1,7,7-trimethyl-bicyclo[2,2,1]heptane as a xylene solution 39.0 g (1.0 mole) of finely powdered sodium amide are added to 800 ml of xylene. The mixture is heated to 50° C., and a solution of 167 g (1.0 mole) of (±)-1,7,7-trimethyl-bicyclo[2,2,1]heptane-2-one-oxime in 200 ml of dimethyl formamide is added. When the gas evolution ceases, 74.5 g (1.0 mole) of propargyl chloride are added to the mixture at the same temperature, and the reaction is continued for further 2 hours. Thereafter the mixture is washed several times with water. The active agent content of the xylene solution is determined by microtitration.

812 g of a xylene solution containing 23.8% of (±)-2-(propargyloxyimino)-1,7,7-trimethyl-bicyclo[2,2,1]heptane are reached; thus the end-product is obtained with a yield of 94.2%.

EXAMPLE 4

Preparation of
(±)-2-(propargyloxyimino)-1,7,7-trimethyl-bicyclo[2,2,1]heptane 59.0 g (0.55 mole) of propargyloxamine hydrochloride are added to a solution of 76 g (0.5 mole) of (±)-1,7,7-trimethyl-bicyclo[2,2,1]heptane-2-one in 225 ml of pyridine and 450 ml of dry ethanol. The reaction mixture is boiled for 3 hours and then it is evaporated in vacuo. The residue is diluted with water, and the aqueous mixture is extracted with dichloroethane. The dichloroethane solution is evaporated, and the residue is subjected to fractional distillation in vacuo. 76.0 g (74.0%) of (±)-2-(propargyloxyimino)-1,7,7-trimethyl-bicyclo[2,2,1]heptane are obtained as a light yellow oil; b.p.: 92° C./1.0 mm Hg, $n_D^{20} = 1.4956$.

EXAMPLE 5

Preparation of
(−)-2-(propargyloxyimino)-1,7,7-trimethyl-bicyclo[2,2,1]heptane

One proceeds as described in Example 4 with the difference that 76.0 g (0.5 mole) of (−)-1,7,7-trimethyl-bicyclo[2,2,1]heptane-2-one are used as starting substance. 79.0 g (77.9%) of (−)-2-(propargyloxyimino)-1,7,7-trimethyl-bicyclo[2,2,1]heptane are obtained; b.p.: 94° C./1.5 mm Hg, $n_D^{20} = 1.4955$, $[\alpha]_D^{20} = -20.02 \pm 1°$ (c=1, methanol).

EXAMPLE 6

Preparation of
(+)-2-(propargyloxyimino)-1,7,7-trimethyl-bicyclo[2,2,1]heptane

One proceeds as described in Example 4 with the difference that 84.0 g (0.5 mole) of (+)-1,7,7-trimethyl-bicyclo[2,2,1]heptane-2-thione are used as starting substance. 81.0 g (79%) of (+)-2-(propargyloxyimino)-1,7,7-trimethyl-bicyclo[2,2,1]heptane are obtained; b.p.: 92° C./1.0 mm Hg, $n_D^{20} = 1.4956$, $[\alpha]_D^{20} = +20.08 \pm 1°$ (c=1, in methanol).

EXAMPLE 7

Preparation of
(+)-2-(propargyloxyimino)-1,7,7-trimethyl-bicyclo[2,2,1]heptane as a xylene solution 40.0 g (1.0 mole) of finely powdered sodium hydroxide and 50 ml of methanol are added to 800 ml of xylene, and the mixture is boiled for 30 minutes under stirring. The mixture is cooled to 30° C., 167.0 g (1.0 mole) of (±)-1,7,7-trimethyl-bicyclo[2,2,1]heptane-2-one-oxime are added, and the mixture is heated slowly to boiling. The methanol and the 18.0 ml (1.0 mole) of water formed in the reaction are removed by distillation through a Marcusson trap. When the removal of water is complete, the reaction mixture is cooled to 30° C., diluted with 200 ml of dimethyl formamide, and 119.0 g (1.0 mole) of propargyl bromide are added dropwise to the mixture. During this operation the temperature of the mixture is maintained at 30° C. be external cooling. The reaction is performed at 30° C. for 2 hours. Thereafter the mixture is washed several times with water, the xylene solution is dried over ignited magnesium sulfate, and its active agent content is determined by microtitration.

835.0 g of a xylene solution containing 23.7% of (+)-2-(propargyloxyimino)-1,7,7-trimethyl-bicyclo[2,2,1]heptane are obtained, which corresponds to a yield of 96.5%.

EXAMPLE 8

Preparation of an emulsifiable concentrate 10 parts by weight of (±)-2-(propargyloxyimino)-1,7,7-trimethyl-bicyclo[2,2,1]heptane are dissolved in 9 parts by weight of xylene, and 1 part by weight of a mixture of an anionic and a non-ionic surfactant (e.g. a 2:3 mixture of Atlox 3386 and Atlox 4851) is added to the solution. The mixture is homogenized. An emulsifiable concentrate containing 50% by weight of active agent (50 EC) is obtained, which can be diluted with water to form a spray liquid.

The optically active compounds can be formulated similarly into emulsifiable concentrates.

EXAMPLE 9

Preparation of microgranulates 26 parts by weight of powdered kaolin, 15 parts by weight of potato starch and/or corn starch and 1 part by weight of talc are homogenized with 5 parts by weight of (±)-2-(propargyloxyimino)-1,7,7-trimethyl-bicyclo[2,2,1]heptane, and 0.5 part by weight of Tween 80 (polyoxyethylene-sorbitane monooleate) are added to the mixture. 2.5 parts by weight of gelatin are swollen in 10 parts by weight of water, then an additional 15 parts by weight of water are added, and the gelatin is dissolved under heating. The resulting solution is admixed with the above powder mixture. The wet mass is homogenized, granulated on a sieve (14 to 16 mesh), the granulates are dried and then sieved again. A microgranular composition containing 10% by weight of active agent is obtained.

The optically active compounds can be converted into microgranular compositions by the same method.

EXAMPLE 10

Preparation of a seed dressing agent 6 parts by weight of a 10% acetone solution of (±)-2-(propargyloxyimino)-1,7,7-trimethyl-bicyclo[2,2,1]heptane are added under stirring to a solution containing 30 parts by weight of acetone, 2.5 parts by weight of hydroxypropyl cellulose, 5 parts by weight of polyethylene glycol (molecular weight: 6000), 20 parts by weight of water and an arbitrary amount of a dyestuff having no germination-inhibiting effect.

The optically active compounds can be converted into seed dressing agents by the same method.

EXAMPLE 11

Preparation of sowing-seed foils (a) 80 g of a polyvinyl alcohol marketed under the trade name RHODOVIOL 4/125 P (viscosity of its 4% aqueous solution is 4 cP at 20° C.; hydrolyzed in 89 mol%) are added under stirring to 615 g of 60° C. water. After dissolution 20 g of a polyvinyl alcohol marketed under the trade name of RHODOVIOL 30/20 M (viscosity of its 4% aqueous solution is 30 cP at 20° C.; hydrolyzed in 98 mol%) and 20 g of glycerol are added, and the mixture is stirred vigorously until a homogeneous solution is formed. After 24 hours of standing, whereupon no more bubbles leave, the solution is smeared onto a glass plate to a thickness of 0.50 mm by doctor-knife casting, and the deposit is dried at room temperature. The resulting foil, 0.05 to 0.06 mm in thickness, separates from the glass plate to give a tough foil easy to handle. This foil is termed in the following as "control foil".

(b) One proceeds as described in point (a) above, with the difference that a solution of 0.120 g of (±)-2-(propargyloxyimino)-1,7,7-trimethyl-bicyclo[2,2,1]heptane in 5 ml of ethanol is also added to the solution of the polymer before casting. After allowing the bubbles to leave, casting and drying the deposit, a foil, similar to that of point (a) but containing 1000 ppm of active agent, is obtained.

(c) One proceeds as described in point (b) with the difference that a solution of 0.0120 g of (±)-2-(propargyloxyimino)-1,7,7-trimethyl-bicyclo[2,2,1]heptane in 5 ml of ethanol is added to the solution to be casted. The resulting foil contains 100 ppm of active agent.

(d) One proceeds as described in point (b) or (c) with the difference that optically active 2-(propargyloxyimino)-1,7,7-trimethyl-bicyclo[2,2,1]heptane is used instead of the racemic compound.

EXAMPLE 12

Examination of plant growth promoting effect (a) Greenhouse tests (a₁) Three cultivation pots were filled with sand, and 30 corn seeds each were sown. 10 of the seeds were not dressed (untreated controls), 10 of the seeds were dressed with a dressing agent described in Example 10 but containing no active agent (placebo), whereas the remaining 10 seeds were dressed with a dressing agent prepared according to Example 10 containing racemic active agent. The cultivation pots were placed in a greenhouse, and the temperature, light and atmospheric humidity of the greenhouse were maintained at optimum. The percentage of germinating seeds was determined, and on the 14th and 28th days after sowing the height and green weight of the emerged plants were measured. The results of the test are summarized in Table 1, in which the percentage of germination is related to the number of seeds sown, whereas the heights and green weights of the plants are given in percentages related to the untreated controls.

TABLE 1

| Treatment | 14th day | | | 28th day | |
|---|---|---|---|---|---|
| | Germination, % | Height, % | Green weight, % | Height, % | Green weight, % |
| Untreated control | 92 | 100 | 100 | 100 | 100 |
| Coated without active agent (placebo) | 95 | 105 | 102 | 103 | 99 |
| Coated with racemic active agent | 95 | 143 | 152 | 148 | 154 |

The data of Table 1 indicate that, within the limits of experimental errors, no difference exists between the untreated controls and the seeds dressed with a composition free of active agent. On the contrary, seedlings higher by 43 to 48% than the two controls emerge from the seeds dressed with the dressing agent according to the invention, and the green weight of these plants exceeds by 52 to 54% that of the controls.

(a₂) Seeds of bean, carrot, flax, green pepper, tomato, spinach, barley and sorghum were sown into cultivation pots (20×20 cm) filled with sand. The cultivation pots were placed in a greenhouse, and treated prior to plant emergence with 0.1 or 0.2 kg of racemic active agent/hectare. The green weights of the 4-week-old plants were measured, and the data were compared to those observed with the untreated controls. The results are summarized in Table 2.

TABLE 2

| Cultivated plant | Green weight in relation to the controls | |
|---|---|---|
| | 0.1 kg/ha | 0.2 kg/ha |
| Bean | 110% | 135% |
| Carrot | 105% | 140% |
| Flax | 118% | 105% |
| Green pepper | 95% | 140% |
| Tomato | 120% | 112% |
| Spinach | 135% | — |
| Barley | 120% | 105% |
| Sorghum | 130% | 130% |

The data of Table 2 indicate that in flax, tomato, spinach and barley cultures the treatment with a dosage of 0.1 kg/hectare provides the better results, whereas in the other cultures a dosage of 0.2 kg/hectare is more favourable. The increase in green weight is 18 to 40% in relation to the untreated controls.

(b) Open-air tests performed on small parcels with dressed seeds

The procedure described in point (a) was repeated with the difference that the seeds were sown in a 10×10 m parcel, the plants were kept under observation for the whole growth season, and the crop yield was also determined. The parcel was hoed in order to remove weeds. The results are given in Table 3.

TABLE 3

| Treatment | Height, % | Green weight, % | Ear yield, % |
|---|---|---|---|
| Untreated control | 100 | 100 | 100 |
| Coated without active agent (placebo) | 98 | 103 | 101 |
| Coated with active agent | 127 | 125 | 120 |

The date of Table 3 demonstrate that the corn emerging from the seeds treated according to the invention are higher by 27%, has a green weight higher by 25%, and provides an ear yield greater by 20% in comparison with the two controls (untreated control and placebo).

(c) Open-air tests performed on small parcels

Corn seeds were sown in small (10×10 m) parcels, and the parcels were treated prior to or after plant emergence with an aqueous spray liquid prepared from the emulsifiable concentrate described in Example 8. The concentrate was diluted with rain water to a final active agent content of 0.02 to 0.1%, depending on the dosage applied, and 500 liters/hectare of the spray liquid were applied. The dosages examined in the pre-emergent treatments varied between 0.1 to 5.0 kg of racemic active agent/hectare, whereas in the post-emergent treatment a dosage of 1 kg of racemic active agent/hectare was applied. The parcels were hoed in order to remove weeds. The results of these tests are summarized in Table 4.

TABLE 4

| Treatment | Dosage, kg of active agent/hectare | Height, % | Green weight, % | Ear yield, % |
|---|---|---|---|---|
| No treatment (untreated | 0 | 100 | 100 | 100 |

TABLE 4-continued

| Treatment | Dosage, kg of active agent/hectare | Height, % | Green weight, % | Ear yield, % |
|---|---|---|---|---|
| | control) | | | |
| Pre-emergent | 0.1 | 105 | 108 | 102 |
| | 1.0 | 121 | 127 | 118 |
| | 3.0 | 127 | 135 | 116 |
| | 5.0 | 115 | 115 | 107 |
| Post-emergent | 1.0 | 116 | 120 | 109 |

The data of Table 4 indicate that the racemic active agent according to the invention, when applied in a pre-emergent treatment, is effective even in a dosage of 0.1 kg/hectare, but the most active dosages are between 1 and 3 kg/hectare. When these latter dosages are applied, the plants are higher by 21 to 27%, have a green weight greater by 27 to 35%, and provide an ear yield greater by 16 to 18% than the untreated controls. The results observed in the post-emergent test, considering the same dosage, are slightly inferior to the former ones.

EXAMPLE 13

Study of insecticidal activity (a) Protection against houseflies (Musca domestica)

The emulsifiable concentrate described in Example 8 was diluted with water to a final active agent content of 3% by weight, and an amount corresponding to 2.5 mg of racemic active agent/cm$^2$ of plane area of the resulting spray liquid was filled into a cylindrical flask. 20 flies, anaesthetized with carbon dioxide, were placed in the flask, the flask was covered with a Petri dish, and the effect of the active agent was observed. In the control test the same dosage of dichlorphon (O,O-dimethyl-2,2-dichlorovinyl phosphate) was applied as active agent.

The results are given in Table 5.

TABLE 5

| | Activity in percents | |
|---|---|---|
| Time (minutes) | Racemic active agent of the invention | Dichlorphon |
| 60 | 68 | 75.2 |
| 120 | 91 | 94.0 |
| 240 | 100 | 100.0 |

(b) Protection against housefly (Musca domestica) larvae 1 kg of wheat barn was admixed with 1 liter of milk, 10 g of fodder yeast and 6 g of Nipagin (ethyl p-hydroxybenzoate) to obtain a culture medium for the cultivation of housefly larvae. 200 g each of the above culture medium were put into small cylindrical flasks, and racemic active agent was added so that the active agent content of the culture medium was 250, 500 and 1000 ppm, respectively. The racemic active agent was introduced in the form of an emulsifiable concentrate containing 50% by weight of the compound concerned, and the culture medium was homogenized with the concentrate. No active agent was introduced into the control flask. 50 one-day-old housefly larvae each were placed in the cylindrical flasks, the flasks were covered with a cloth ensuring good ventilation, and the percentage of images developing from the pupae was determined in relation to the control. The results are given in Table 6.

TABLE 6

| Treatment | Dosage, ppm | Development, % | Activity, % |
|---|---|---|---|
| Untreated control | — | 100.0 | 0 |
| Treated with racemic | 250 | 29.6 | 70.4 |
| active agent | 500 | 0 | 100.0 |
| | 1000 | 0 | 100.0 |

The above test results show that on houseflies the active agent according to the invention exerts approximately the same effect as dichlorphon, a known insecticide. Although the effect is slower on more resistant test insects, the new compound of the formula (I) is superior to the known active agent with respect to its lower toxicity and the absence of cholinesterase blocking effect.

EXAMPLE 14

Protection against dried bean beetle (Acanthoscelides obtectus)

The procedure described in point (a) of Example 13 was repeated with the difference that dried bean beetles were used as test insects. The results are given in Table 7.

TABLE 7

| | Activity in percents | |
|---|---|---|
| Time (minutes) | Racemic active agent of the invention | Dichlorphon |
| 60 | 17.5 | 47 |
| 120 | 35.0 | 72 |
| 240 | 65.5 | 100 |
| 1440 | 100.0 | 100 |

(b) 100 g of bean seeds each were treated with a spray liquid containing 1.0% by weight of racemic active agent (prepared by diluting an emulsifiable concentrate containing 50% by weight of active agent) in an amount corresponding to 250, 500 and 1000 ppm of active agent, respectively. The control seeds were not treated. The seeds were put into small cylindrical flasks. 20 insects each were placed in the flasks, and the flasks were covered with a cloth. After 14 days the survivors were counted. The results, expressed in percentages of the control, are given in Table 8.

TABLE 8

| Treatment | Dosage, ppm | Survivors, % | Activity, % |
|---|---|---|---|
| Untreated control | — | 100 | 0 |
| Treated with racemic | 250 | 5 | 95 |
| active agent | 500 | 0 | 100 |
| | 1000 | 0 | 100 |

The data of Table 8 indicate that the active agent can be applied successfully to kill granarial insect pests, such as dried bean beetle, even in a concentration of 250 ppm.

What we claim is:

1. A plant growth promoting composition comprising as active agent 0.001 to 98% by weight of racemic and/or optically active 2-(propargyloxyimino)-1,7,7-trimethyl-bicyclo[2,2,1]heptane of the formula (I),

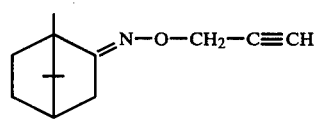

(I)

along with a conventional inert diluent.

* * * * *